United States Patent
Lin et al.

(10) Patent No.: US 6,338,752 B1
(45) Date of Patent: Jan. 15, 2002

(54) α-TCP/HAP BIPHASIC CEMENT AND ITS PREPARING PROCESS

(75) Inventors: Feng-Huei Lin; Chun-Jen Liao, both of Taipei (TW)

(73) Assignee: Purzer Pharmaceutical Co., Ltd. (TW)

(*) Notice: Subject to any disclaimer, the term of this patent is extended or adjusted under 35 U.S.C. 154(b) by 0 days.

(21) Appl. No.: 09/553,176

(22) Filed: Apr. 20, 2000

(51) Int. Cl.⁷ .............................................. C04B 12/02
(52) U.S. Cl. ............................ 106/35; 106/670; 501/1; 423/311; 423/315; 423/305
(58) Field of Search .................... 106/35, 670; 501/1; 423/311, 315, 305

(56) References Cited

U.S. PATENT DOCUMENTS

| | | | |
|---|---|---|---|
| 4,938,938 A | * | 7/1990 | Ewers et al. ................ 423/308 |
| 5,017,518 A | * | 5/1991 | Hirayama et al. ............. 501/1 |
| 5,180,426 A | * | 1/1993 | Sumita et al. ................ 106/35 |
| 5,238,491 A | * | 8/1993 | Sughara et al. ............... 106/35 |

* cited by examiner

Primary Examiner—C. Melissa Koslow
(74) Attorney, Agent, or Firm—Lowe Hauptman Gilman & Berner, LLP

(57) ABSTRACT

A biphasic cement of α-TCP/HAP is primarily composed of 30–60 wt % α-tricalcium phosphate ($Ca_3(PO_4)_2$, α-TCP) and 40–70 wt % of hydroxyapatite ($Ca_{10}(PO_4)_6(OH)_2$, HAP). The biphasic cement of α-TCP/HAP of the present invention is superior since it can set rapidly while soaking in a water solution. The present invention also provides a process for preparing the biphasic cement of α-TCP/HAP, in which the composition of the biphasic cement of α-TCP/HAP can be controlled.

12 Claims, 1 Drawing Sheet

α-TCP/HAP BIPHASIC CEMENT AND ITS PREPARING PROCESS

FIELD OF THE INVENTION

The present invention relates to a bone filling material biphasic cement of α-TCP/HAP and its process for preparing.

BACKGROUND OF THE INVENTION

For those who have to remove partial bone because of traumas, bone tumors or cysts, proper bone filling materials or cement are necessary to remedy the defect.

Conventional bone filling cement is made from polymers such as acrylic resin and HDPE, but the polymers are not biocompaible with human beings. In view of this, some researchers therefore added calcium phosphates (CPs) into the polymers to improve their biocompatibility, because the CPs such as hydroxyapatite powder ($Ca_{10}(PO_4)_6(OH)_2$, HAP) or tricalcium phosphate powder ($Ca_3(PO_4)_2$, TCP) are more biocompatible and can directly bind with bone tissue of human bodies. However, the CP powder tended to be enveloped by the polymers, which limited the effects since the CPs couldn't contact with the bone tissue.

Consequently many researchers try to develop the bone filling material only composed of inorganic CPs, e.g., calcium phosphate cement (CPC), because of their better biocompatibility and similar components to human beings'. So far, many CPC systems are being developed, such as tetracalcium phosphate ($Ca_4P_2O_9$, TTCP), dicalcium phosphate ($CaHPO_4$, DCP), octacalcium phosphate ($Ca_8H_2(PO_4)_6 \cdot 5H_2O$, OCP), α-TCP, β-TCP and HAP.

In view of the development of bone filling materials, the ideal bone filling materials should (a) contain CPs because of its better biocompatibility, (b) provide plasticity at an earlier stage of the filling surgery, and (c) be able to rapidly set after being filled into the defective parts.

SUMMARY OF THE INVENTION

The object of the present invention is to provide a biphasic bone filling material of α-TCP/HAP, which is a kind of calcium phosphate cement (CPC), and can be plastic powder and set rapidly so that it is fit for bone filling surgery.

It is another object of the present invention to provide a process for preparing biphasic cement of α-TCP/HAP, in which a superior bone filling material can be obtained.

It is still another object of the present invention to provide a process for preparing biphasic cement of α-TCP/HAP, in which the composition of biphasic cement of α-TCP/HAP can be controlled.

Biphasic cement of α-TCP/HAP in the present invention primarily comprises α-tricalcium phosphate ($Ca_3(PO_4)_2$, α-TCP) and hydroxyapatite ($Ca_{10}(PO_4)_6(OH)_2$, HAP). Biphasic cement of α-TCP/HAP in the present invention has a preferred composition as 30–60 wt % of α-TCP and 70–40 wt % of HAP.

Biphasic cement of α-TCP/HAP in the present invention is a kind of calcium phosphate cement (CPC), which can set in human body because different kinds of CPs can be dissolved in water solution and perform segregation. Apatite crystal generated in segregation can interactively set with each other similar to the coagulation of cement. Biphasic cement of α-TCP/HAP in the present invention is a superior cement since it can set rapidly while soaking in water solution.

The process for preparing biphasic cement of α-TCP/HAP in the present invention is to bring the powder mixture of ammonium phosphate (AP) and hydroxyapatite (HAP) to thermal process, and then biphasic cement of α-TCP/HAP is obtained. In the process of the present invention, the composition of biphasic cement of α-TCP/HAP can be controled by adjusting the weight percentage of AP powder and HAP powder respectively.

DETAILED DESCRIPTION OF THE PREPERRED EMBODIMENT

Figure 1:
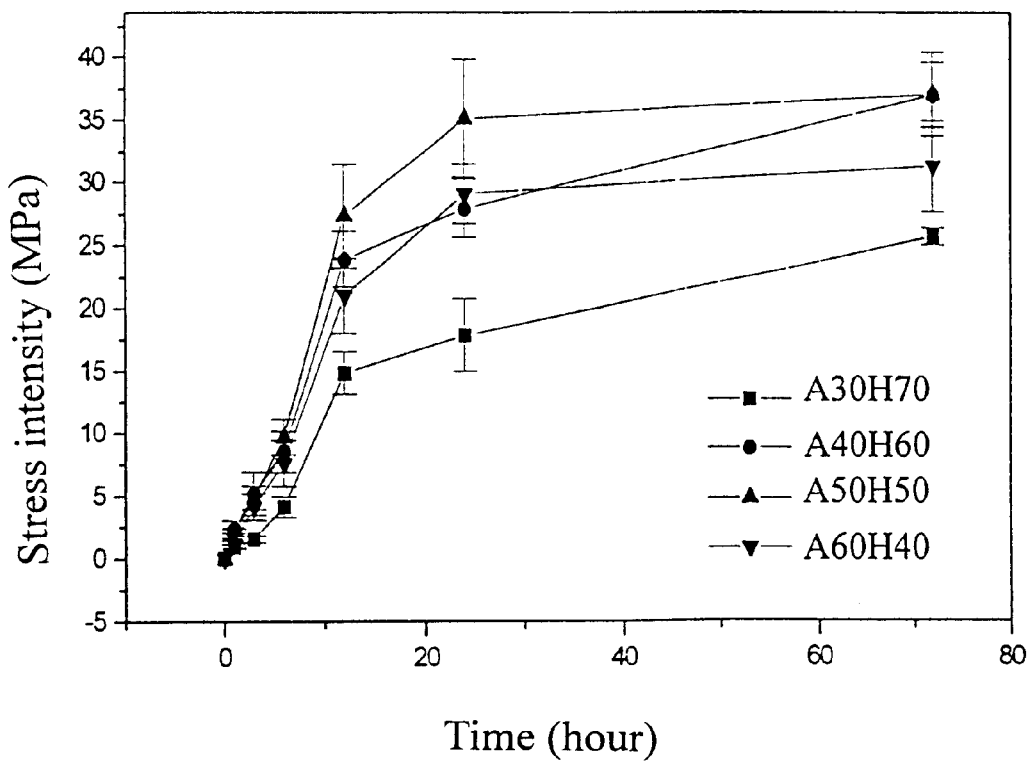
FIG. 1 shows the stress intensity of the cement samples of H7A3, H6A4, H5A5 and H4A6 after soaked for different times.

The process for preparing biphasic cement of α-TCP/HAP in the present invention is to bring the powder mixture of the AP powder and the HAP powder to thermal process, and then biphasic cement of α-TCP/HAP is obtained.

In the present invention, the powder mixture is prepared by dissolving the AP powder in deionized water, and then adding the HAP powder into the solution. After stirring, the mixture is dried in an oven. Since the processing steps are pretty simple, the composition of the AP powder and the HAP powder in the mixture can be controlled arbitrarily and precisely.

The thermal processing of the powder mixture is to heat the powder mixture to 1,200° C.–1,500° C. at a heating rate of 10° C./min and keep it isothermal at 1,200° C.–1,500° C. for one hour. Then the mixture is quenched to room temperature, and the biphasic cement of α-TCP/HAP is obtained.

In the present invention, the HAP powder can be mixed well with the AP powder because the AP powder can be dissolved in water solution. When the mixture is heated to high temperature, the $HPO_4^{2-}$ from the AP can react with the HAP to produce the biphasic TCP/HAP. Furthermore, different and precise weighing compositions of α-TCP/HAP can be obtained by adjusting the amount of the AP powder. In the process of the present invention, the preferred composition of the powder mixture is to contain 4–8 wt % of the AP powder and 92–96 wt % of the HAP powder.

The biphasic composition of the α-TCP and HAP in the present invention is an important factor to influence the systematic dissolution and segregation rate of the cement. According to the process of the present invention, the properties of biphasic cement of α-TCP/HAP can be controlled and changed by changing the weight ratio of α-TCP/HAP.

More detailed examples are used to illustrate the present invention, and these examples are used to explain the present invention. The examples below, which are given simply by way of illustration, must not be taken to limit the scope of the invention.

EXAMPLE 1

0.219 g of AP powder was weighed and dissolved in deionized water. Then 20 g of HAP powder was added into the AP solution and mixed well by stirring, then dried at 70° C. in an oven for three days. The dried powder mixture of the AP and the HAP was placed in a platinum crucible and sent into an SiC furnace to be heated to 1,350° C. at a programmed heating rate of 10° C./min and kept isothermal at 1,350° C. for one hour, which then was quenched to room temperature. Biphasic cement of α-TCP/HAP with a weighing ratio of 10/90 (abbreviated as A10H90) was thus obtained.

EXAMPLE 2 TO EXAMPLE 9

The procedures were similar to the example 1, but the AP powder was added by different weight to obtain different products including A20H80, A30H70, A40H60, A50H50, A60H40, A70H30, A80H20 and A90H10, which are listed in Table 1:

TABLE 1

| Example | Weight of HAP (g) | Weight of AP (g) | wt % of α-TCP/HAP | Product |
| --- | --- | --- | --- | --- |
| 1 | 20 | 0.219 | 10/90 | A10H90 |
| 2 | 20 | 0.438 | 20/80 | A20H80 |
| 3 | 20 | 0.657 | 30/70 | A30H70 |
| 4 | 20 | 0.876 | 40/60 | A40H60 |
| 5 | 20 | 1.095 | 50/50 | A50H50 |
| 6 | 20 | 1.314 | 60/40 | A60H40 |
| 7 | 20 | 1.533 | 70/30 | A70H30 |
| 8 | 20 | 1.752 | 80/20 | A80H20 |
| 9 | 20 | 1.971 | 90/10 | A90H10 |

Test 1

The biphasic cement of α-TCP/HAP obtained in example 3 was ground by aluminum oxide in a grinder so the diameter of the cement was reduced between 0.5 μm and 2 μm. The ground powder was then mixed with $Na_2HPO_4$ solution with a concentration of 0.4 ml/g or 2.5%, and was extruded from a stainless steel extruder to obtain several cylindrical samples which had a diameter of 0.7 cm and a height of 1.4 cm. The extruded samples were then placed in saturated steam for 1–5 minutes, and moved into Ringer solution to observe the setting phenomenon. The results observed are listed in Table 2.

Test 2 to Test 4

The procedures were similar to the Test 1, but the biphasic cement samples of α-TCP/HAP obtained from Example 4 to Example 6 were used instead. The results observed are also listed in Table 2.

TABLE 2

| sample | 1 minute | 2 minutes | 3 minutes | 4 minutes |
| --- | --- | --- | --- | --- |
| A30H70 | NS | NS | S | S |
| A40H60 | NS | S | S | S |
| A50H50 | NS | S | S | S |
| A60H40 | NS | NS | S | S |

S: setting
NS: no setting

Table 2 shows that the biphasic cement samples of α-TCP/HAP set or not when moved into the Ringer solution after placed in saturated steam for different periods of time. Both the A30H70 and the A60H40 didn't set when moved into the solution after placed in steam for 2 minutes, but set at 3 minutes. The A40H60 and A50H50 set in shorter time when placed in steam for 2 minutes. The results in Table 2 showed that the cement of the present invention can set in a very short time.

Test 5 to Test 8

The samples of A30H70, A40H60, A50H50 and A60H40 were soaked in Ringer solution at a temperature of 37° C. for 1 hour, 3 hours, 6 hours, 12 hours 24 hours, 3 days and 7 days, respectively. The samples were picked out from the solution at different times and moved into acetone to stop the reaction. The soaked samples were then measured by MTS to record their stress intensity. The results are shown as FIG. 1.

FIG. 1 shows that the stress intensity of A50H50 achieves 35 MPa after soaking for 24 hours. The other samples could also approximate a similar level, e.g., the all biphasic cement of α-TCP/HAP in the present invention can sustain high stress.

From the foregoing description, one skilled in the art can easily ascertain the essential characteristics of this invention, and, without departing from the scope thereof, can make various changes and modifications of the invention to adapt it to various usages and conditions. Thus, other embodiments are also within the claims.

What is claimed is:

1. A process for preparing biphasic cement of α-TCP/HAP, comprising the steps of:

(a) forming a powder mixture of ammonium phosphate powder and hydroxyapatite powder; and (b) thermal processing the powder mixture wherein the powder mixture contains the AP powder in an amount of 4% to 8% by weight, and the HAP powder in an amount of 92% to 96% by weight.

2. The process of claim 1, wherein the powder mixture is prepared by dissolving the AP powder in deionized water, and then the HAP powder is added and stirred in the solution, the solution mixture then is dried.

3. The process of claim 1, wherein the thermal processing in step (b) is to heat the powder mixture to 1,200° C.–1,500° C. at a heating rate of 10° C./min and keep it isothermal at 1,200° C.–1,500° C. for one hour, and then the heated mixture then is quenched to room temperature.

4. The process of claim 1, wherein the biphasic cement of α-TCP/HAP contains the α-TCP in the amount of 30% to 60% by weight, and the HAP in the amount of 40% to 70% by weight.

5. A process for preparing biphasic cement of α-TCP/HAP, comprising the steps of:

(a) forming a powder mixture of ammonium phosphate powder and hydroxyapatite powder; and (b) thermal processing the powder mixture wherein the powder mixture is prepared by dissolving the AP powder in deionized water, and then the HAP powder is added and stirred in the solution, the solution mixture then is dried.

6. The process of claim 5, wherein the powder mixture contains the AP powder in an amount of 4% to 8% by weight, and the HAP powder in an amount of 92% to 96% by weight.

7. The process of claim 5, wherein the thermal processing in step (b) is to heat the powder mixture to 1,200° C.–1,500° C. at a heating rate of 10° C./min and keep it isothermal at 1,200° C.–1,500° C. for one hour, and then the heated mixture then is quenched to room temperature.

8. The process of claim 5, wherein the biphasic cement of α-TCP/HAP contains the α-TCP 30% to 60% by weight, and the HAP 40% to 70% by weight.

9. A process for preparing biphasic cement of α-TCP/HAP, comprising the steps of:
   (a) forming a powder mixture of ammonium phosphate powder and hydroxyapatite powder; and
   (b) thermal processing the powder mixture wherein the thermal processing in step (b) is to heat the powder mixture to 1,200° C.–1,500° C. at a heating rate of 10° C./min and keep it isothermal at 1,200° C.–1,500° C. for one hour, and then the heated mixture then is quenched to room temperature.

10. The process of claim 9, wherein the powder mixture contains the AP powder in the amount of 4% to 8% by weight, and the HAP powder in an amount of 92% to 96% by weight.

11. The process of claim 9, wherein the powder mixture is prepared by dissolving the AP powder in deionized water, and then the HAP powder is added and stirred in the solution, the solution mixture then is derived.

12. The process of claim 9, wherein the biphasic cement of α-TCP/HAP contains the α-TCP 30% to 60% by weight, and the HAP 40% to 70% by weight.

* * * * *